(12) United States Patent
Butler

(10) Patent No.: US 9,993,270 B2
(45) Date of Patent: Jun. 12, 2018

(54) BONE FASTENER AND METHODS OF USE

(71) Applicant: Warsaw Orthopedic, INc., Warsaw, IN (US)

(72) Inventor: Brian Butler, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days. days.

(21) Appl. No.: 14/334,970

(22) Filed: Jul. 18, 2014

(65) Prior Publication Data

US 2016/0015429 A1 Jan. 21, 2016

(51) Int. Cl.
*A61B 17/70* (2006.01)

(52) U.S. Cl.
CPC ................................ *A61B 17/7035* (2013.01)

(58) Field of Classification Search
CPC ............ A61B 17/7032; A61B 17/7005; A61B 17/7037; A61B 17/7076; A61B 17/7082; A61B 17/7034; A61B 17/7086; A61B 17/7091; A61B 17/8605; A61B 17/7038; A61B 17/7067; A61B 17/7035
USPC .................................. 606/246–279, 300–328
See application file for complete search history.

(56) References Cited

U.S. PATENT DOCUMENTS

| | | | | |
|---|---|---|---|---|
| 6,063,090 A * | 5/2000 | Schlapfer | ........... | A61B 17/7041 606/270 |
| 7,722,652 B2 * | 5/2010 | Justis | ................. | A61B 17/7035 606/267 |
| 8,308,782 B2 * | 11/2012 | Jackson | ............. | A61B 17/7008 606/305 |
| 8,444,681 B2 * | 5/2013 | Jackson | ............. | A61B 17/7032 606/300 |
| 9,084,634 B1 * | 7/2015 | Lab | ..................... | A61B 17/7038 |
| 9,168,069 B2 * | 10/2015 | Jackson | ............. | A61B 17/7037 |
| 2007/0093826 A1 * | 4/2007 | Hawkes | ............. | A61B 17/7032 606/279 |
| 2008/0015579 A1 * | 1/2008 | Whipple | ............ | A61B 17/7037 606/250 |
| 2010/0152787 A1 * | 6/2010 | Walsh | ................ | A61B 17/7037 606/308 |
| 2012/0209336 A1 * | 8/2012 | Jackson | ............. | A61B 17/7032 606/305 |
| 2013/0110180 A1 * | 5/2013 | Doubler | ............. | A61B 17/7037 606/308 |
| 2013/0144346 A1 * | 6/2013 | Jackson | ............. | A61B 17/8605 606/305 |
| 2015/0119940 A1 * | 4/2015 | Jackson | ............. | A61B 17/7076 606/266 |
| 2015/0173816 A1 * | 6/2015 | Biedermann | ...... | A61B 17/8605 606/308 |

* cited by examiner

*Primary Examiner* — Pedro Philogene

(57) ABSTRACT

A bone fastener includes a first portion that defines a longitudinal axis and includes an inner surface defining an implant cavity. A second portion that includes a first end and a second end configured to penetrate tissue. A retainer includes a wall having a first end surface and a second end surface. The wall including at least one first elongated cavity and at least one second elongated cavity. The first cavity includes a gap of the first end surface and the second cavity including a gap of the second end surface. The wall further includes an inner surface disposed about the first end. Systems and methods are disclosed.

17 Claims, 7 Drawing Sheets

BONE FASTENER AND METHODS OF USE

TECHNICAL FIELD

The present disclosure generally relates to medical devices for the treatment of spinal disorders, and more particularly to a surgical implant system including a bone fastener that provides stabilization while reducing stress on spinal elements.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, a bone fastener is provided. The bone fastener includes a first portion that defines a longitudinal axis and includes an inner surface defining an implant cavity. A second portion that includes a first end and a second end configured to penetrate tissue. A retainer includes a wall having a first end surface and a second end surface. The wall including at least one first elongated cavity and at least one second elongated cavity. The first cavity includes a gap of the first end surface and the second cavity including a gap of the second end surface. The wall further includes an inner surface disposed about the first end. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
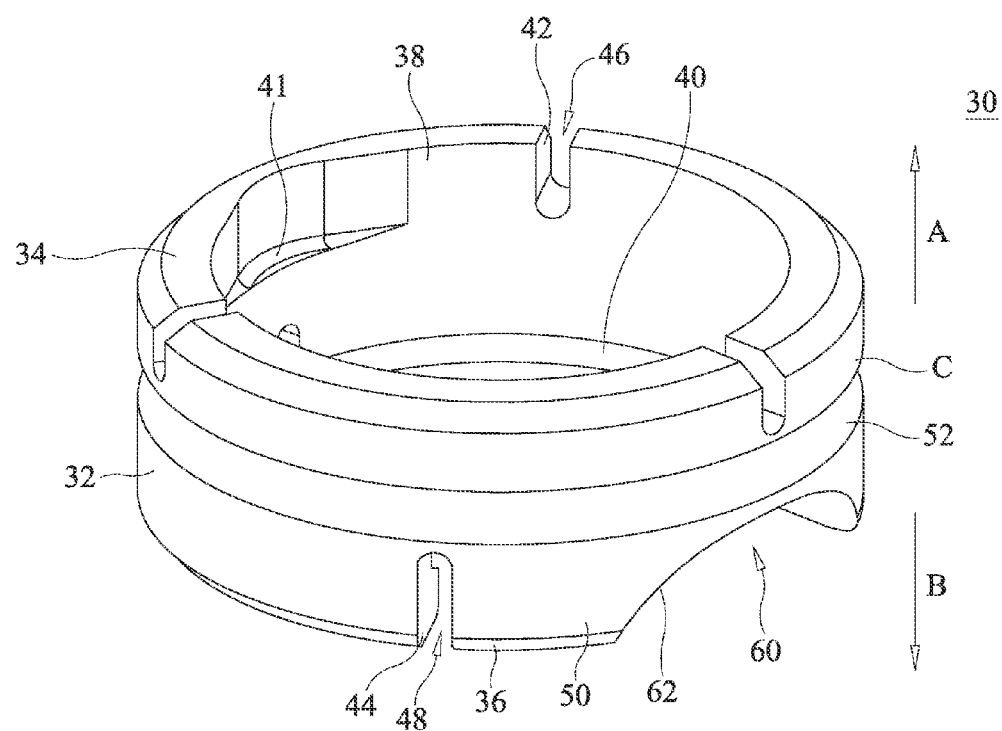
FIG. 1 is a perspective view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In some embodiments, the spinal implant system includes a bone fastener comprising a biased screw design. In some embodiments, the spinal implant system includes retainer configured to assemble a screw of the bone fastener into a receiver assembly. In one embodiment, the system includes a cylindrical post having a boss that allows for fixing the post to a spherical head.

In one embodiment, the system includes a bone fastener including a spherical ring retainer having mating elements that engage a radial flange of a cylindrical post of a bone screw shaft. In some embodiments, the ring retainer engages the post of the shaft in a flexible fit, snap fit, interference fit and/or friction fit. In one embodiment, the ring retainer has a cut-out, such as, for example, a side slot. In one embodiment, the ring retainer has a plurality of side slots. In one embodiment, the ring retainer has a C-ring configuration. In one embodiment, the ring retainer has a collet configuration configured to snap onto a cylindrical bone screw having a radial flange. In one embodiment, the ring retainer comprises halves. In one embodiment, the ring retainer has a clam shell configuration.

In one embodiment, the system includes a bone fastener including a retainer, such as, for example, a carrier having mating elements that engage a post of a bone screw shaft. In one embodiment, the carrier is configured to snap and/or wrap around the post. In one embodiment, the carrier is configured for use without a ring retainer to hold a post of a bone screw shaft with a receiver and/or sub-assembly. In one embodiment, the carrier is configured to snap over a bone screw sphere. In one embodiment, the carrier is split into pieces or halves.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-4, there are illustrated components of a spinal implant system 10 including a bone fastener 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 3:
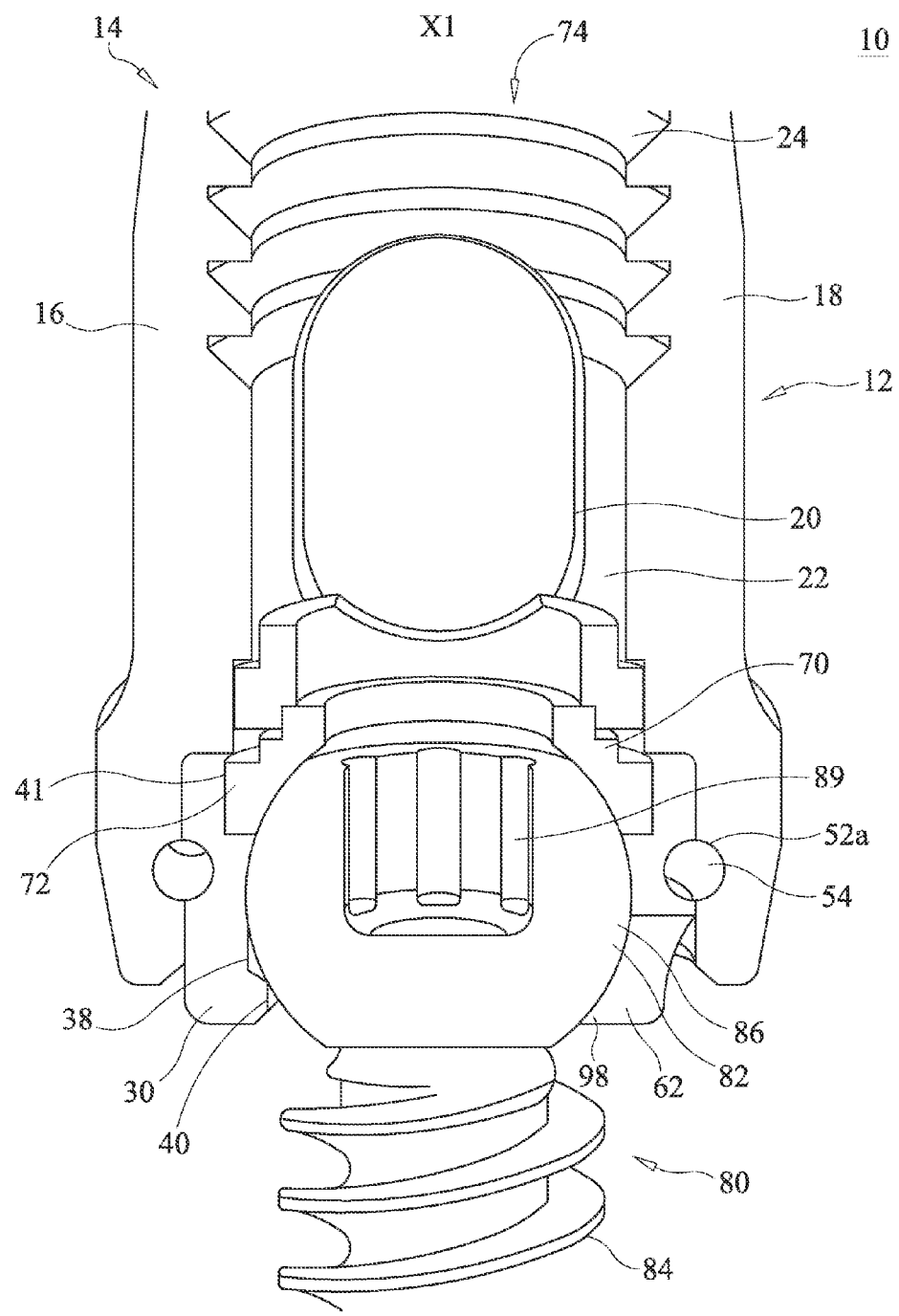
FIG. 3 is a side, cross section view of components of one embodiment of a spinal implant system in accordance with the principles of the present disclosure.

System 10 includes an implant, such as, for example, bone fastener 12, as shown in FIG. 3. Fastener 12 includes a portion, such as, for example, a receiver 14 having a closed proximal end and extending along an axis X1. Receiver 14 includes a pair of spaced apart arms 16, 18 that connect with the closed proximal end and define an implant cavity 20 therebetween configured for disposal of at least a portion of a spinal construct, which includes, such as, for example, a spinal rod. Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an outer surface extending between a pair of side surfaces of receiver 14. At least one of the outer surfaces and the side surfaces of arms 16, 18 have at least one recess or cavity configured to receive an insertion tool, compression instrument and/or instruments for inserting and tensioning fastener 12. In some embodiments, receiver 14 includes an open proximal end that communicates with implant cavity 20 and is configured for passage of a spinal construct therethrough.

Cavity 20 is substantially cylindrical. In some embodiments, all or only a portion of cavity 20 may have alternate cross section configurations, such as, for example, V-shaped, W-shaped, oval, oblong triangular, square, polygonal, irregular, uniform, non-uniform, offset, staggered, and/or tapered. Cavity 20 includes an inner surface 22. Surface 22 includes a thread form 24 configured for engagement with a coupling member, such as, for example, a setscrew (not shown), to retain a spinal rod within cavity 20. In some embodiments, the inner surface of receiver 14 may be disposed with the coupling member in alternate fixation configurations, such as, for example, friction fit, pressure fit, locking protrusion/recess, locking keyway and/or adhesive.

Receiver 14 comprises a sub-assembly that includes a retainer, such as, for example, a carrier 30, as shown in FIG. 1. Carrier 30 is assembled with receiver 14 as part of a sub-assembly of fastener 12 and for connecting receiver 14 with a second portion, such as, for example, a shaft 80 of fastener 12.

Carrier 30 includes a wall 32 having an end surface 34 and an end surface 36. End surfaces 34, 36 each have a planar surface configuration. Wall 32 includes an inner surface 38. Surface 38 defines a circumferential flange 40 configured for engagement with a spherical head 82 of shaft 80 and retention of head 82 with carrier 30, as described herein. Surface 38 defines a recess 41 configured for disposal of a crown, as discussed herein. In some embodiments, all or only a portion of surface 38 may have alternate surface configurations to enhance engagement with shaft 80 such as, for example, rough, arcuate, undulating, mesh, porous, semi-porous, dimpled and/or textured.

Wall 32 includes a surface that defines a plurality of elongated cavities, such as, for example, slots 42 disposed circumferentially about wall 32. Each of slots 42 extend transversely entirely through a thickness of wall 32. Each of slots 42 extend axially through only a portion of wall 32 in a parallel orientation relative to axis X1. Slots 42 are spaced equidistantly about a circumference C of wall 32. Slots 42 extend through wall 32 in a U-shaped configuration, in the direction shown by arrow A in FIG. 1, to an opening, such as, for example, a gap 46 aligned with surface 34. Wall 32 includes a plurality of gaps 46 equidistantly spaced about circumference C.

The surface of wall 32 also includes a plurality of elongated cavities, such as, for example, slots 44 disposed circumferentially about wall 32. Each of slots 44 extend transversely entirely through the thickness of wall 32. Each of slots 44 extend axially through only a portion of wall 32 in a parallel orientation relative to axis X1. Slots 44 are spaced equidistantly about circumference C of wall 32. Slots 44 extend through wall 32 in a U-shaped configuration, in the direction shown by arrow B in FIG. 1, to an opening, such as, for example, a gap 48 aligned with surface 36. Wall 32 includes a plurality of gaps 48 equidistantly spaced about circumference C. Slots 42 are offset and disposed in axial non-alignment with slots 44. In some embodiments, slots 42, 44 are disposed in axial alignment. In some embodiments, slot 42 extends to gap 46 in a direction opposite to the direction that slot 44 extends to gap 48.

In some embodiments, wall 32 may include one or a plurality of slots 42 and/or slots 44. In some embodiments, the depth and/or thickness of slots 42 and/or slots 44, individually or collectively, may vary. In some embodiments, slots 42 and/or slots 44 may be non-equidistantly spaced about circumference C. In some embodiments, slots 42 may extend in various orientations relative to axis X1, slots 44 and/or wall 32, such as, for example, perpendicular, transverse, angular, offset and/or staggered.

Carrier 30 is disposed with receiver 14, as described herein, in a configuration that facilitates assembly of receiver 14 with shaft 80. In some embodiments, carrier 30 engages shaft 80 in a flexible fit, snap fit, interference fit and/or friction fit. Slots 42, 44 provide carrier 30 with flexibility so that wall 32 can flex and/or move about a surface 86 of head 82 for disposal of head 82 with flange 40 to retain shaft 80 with the sub-assembly, which includes carrier 30, of receiver 14. In some embodiments, all or only a portion of carrier 30 may have a flexible or elastic configuration, and/or have elastic and/or flexible properties such as the elastic and/or flexible properties corresponding to the material examples described above.

Carrier 30 is mounted as a sub-assembly with receiver 14. The receiver 14/carrier 30 sub-assembly is manipulated for assembly with shaft 80 such that carrier 30 translates along axis X1 over shaft 80. As wall 32 engages shaft 80, surface 38 engages surface 86 such that gaps 46, 48 avow slots 42, 44 to expand. Wall 32 flexes about head 82 to an expanded orientation such that carrier 30 snap fits in a mating engagement with shaft 80. Wall 32 is flexible and resiliently biased to its original orientation for disposal of head 82 in an abutting engagement with flange 40. A crown 70 of the sub-assembly of receiver 14 is disposable in recesses 41 to engage head 82 and fix shaft 80 with carrier 30.

Carrier 30 includes an outer surface 50 that defines a circumferential cavity 52, as shown in FIG. 1. Surface 50 and receiver 14 define a cavity 52a that is configured for disposal of an elastic ring 54 disposed with receiver 14. Cavity 52 is aligned with a cavity disposed with receiver 14 to enclose ring 54.

Shaft 80 includes head 82 disposed with surface 38 and a threaded end 84, as shown in FIG. 3, configured to penetrate tissue, such as, for example, bone. End 84 is rotatable relative to axis X1. In some embodiments, head 82 rotates relative to carrier 30. In some embodiments, head 82 is fixed with carrier 30. In some embodiments, receiver 14 is rotatable relative to shaft 80 about axis X1 in a range of 0-180 degrees. In one embodiment, receiver 14 is rotatable relative to shaft 80 to a selected angle about axis X1 and/or to a maximum angle such that end 84 is disposed to engage a concave surface of carrier 30 that defines an opening 98.

Figure 4:
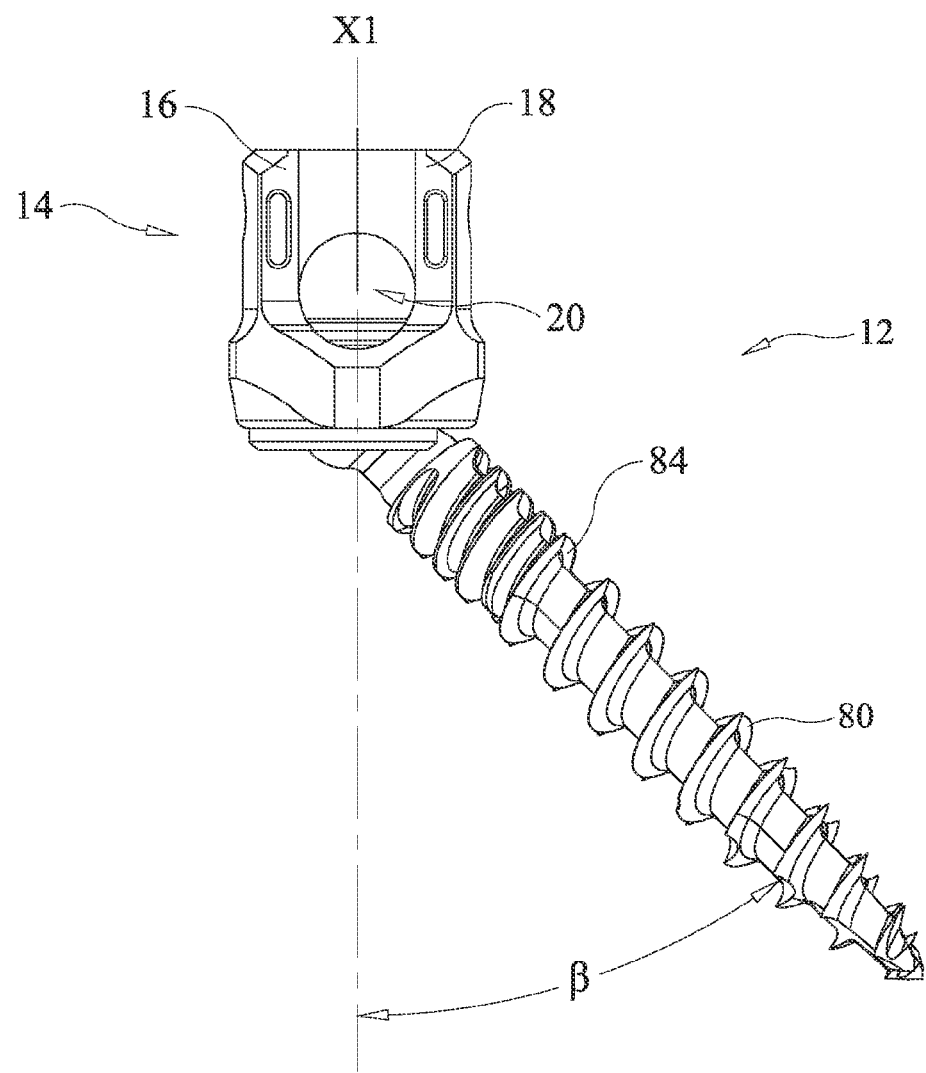
FIG. 4 is a side view of the components shown in FIG. 3.

In some embodiments, end 84 is movable relative to receiver 14 between a first orientation in which shaft 80 is coaxial with axis X1, as shown in FIG. 3, and a second orientation in which end 84 is movable through an angular range, for example, angular range β, of greater than 0 degrees through about 45 degrees relative to axis X1, as shown in FIG. 4. In some embodiments, end 84 is rotatable in a plurality of planes that lie in a cone configuration about receiver 14 that defines a range of motion of end 84 about axis X1. In one embodiment, end 84 is rotatable to a selected angle within angular range β in a sagittal plane of a body of a patient. In one embodiment, end 84 is rotatable to a selected angle within angular range β in a transverse plane of the body. In one embodiment, end 84 is rotatable to a selected angle within angular range β in a coronal plane of the body.

Head 82 includes a socket 89 having a hexalobe geometry configured for disposal of a similarly shaped bit of a tool, such as, for example, a driver. The driver engages the surfaces of socket 89 to rotate shaft 80. Socket 89 is in communication with an opening 74 and cavity 20 such that a driver may be inserted between arms 16, 18 and translated axially until the bit of the driver is disposed in socket 89. In some embodiments, socket 89 has a cruciform, phillips, square, hexagonal, polygonal, star or hexalobe cross sectional configuration for disposal of a correspondingly shaped portion of a driver.

Figure 2:
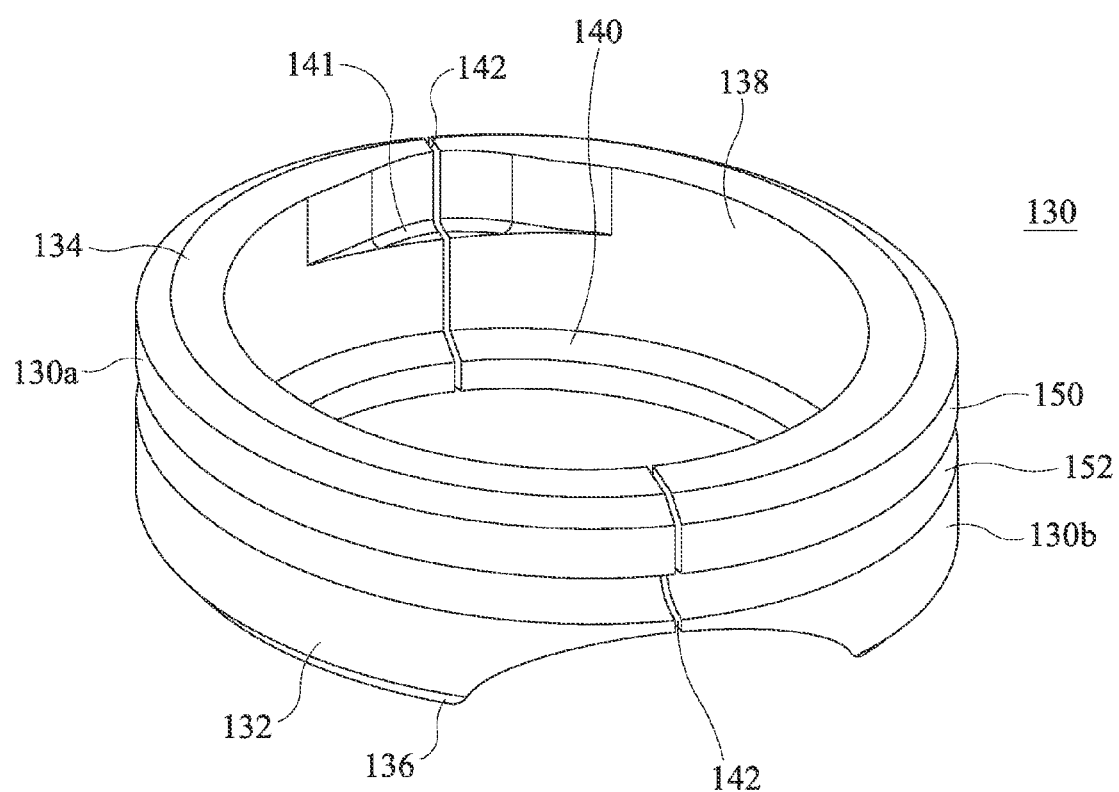
FIG. 2 is a perspective view of components of one embodiment of a spinal implant system in accordance with the principles of the present disclosure.

In one embodiment, as shown in FIG. 2, the sub-assembly, similar to that described herein, of receiver 14 includes a retainer, such as, for example, a carrier 130, similar to carrier 30 described with regard to FIGS. 1, 3 and 4. Carrier 130 is assembled with receiver 14 as a sub-assembly of fastener 12 and for connecting receiver 14 with shaft 80, similar to that described herein.

Carrier 130 includes a wall 132, similar to wall 32 described herein, having an end surface 134 and an end surface 136. Wall 132 includes an inner surface 138 and defines a circumferential flange 140 configured for engagement with head 82, as described herein. Surface 138 defines a recess 141 configured for disposal of crown 70, as discussed herein.

Wall 132 includes a surface that defines a plurality of elongated cavities, such as, for example, slots 142, similar to slots 42, 44 described herein, disposed diametrically about wall 132. Each of slots 142 extend transversely entirely through a thickness of wall 132. Each of slots 142 extend axially entirely through wall 132 in a parallel orientation relative to axis X1. Slots 142 extend through wall 32 to define a gap with surfaces 134, 136. Slots 142 extend entirely through wall 132 such that carrier 130 includes a pair of separate carrier components 130a, 130b that comprise halves of the retainer that are engaged and/or wrapped about head 82. Components 130a, 130b are disposed about head 82 such that a surface of radial flange 140 engages surface 86. Carrier 130 is disposed with receiver 14, as described herein, in a configuration that facilitates assembly of receiver 14 with shaft 80.

Carrier 130 is mounted as a sub-assembly with receiver 14. The receiver 14/carrier 130 sub-assembly is manipulated for assembly with shaft 80 such that components 130a, 130b are engaged over head 82. Carrier 130 fits in a mating engagement with shaft 80 such that head 82 is disposed in an abutting engagement with flange 140. Crown 70 of the sub-assembly of receiver 14 is disposable in recesses 141 to engage head 82 and fix shaft 80 with carrier 130. Carrier 30 includes an outer surface 150 that defines a circumferential cavity 152, similar to cavity 52 described herein.

In assembly, operation and use, spinal implant system 10, similar to the systems and methods described herein, includes fastener 12 and is employed with a surgical procedure for treatment of a spinal disorder affecting a section of a spine of a patient, as discussed herein. Spinal implant system 10 is employed with a surgical procedure for treatment of a condition or injury of an affected section of the spine.

In use, to treat the affected section of the spine, a medical practitioner obtains access to a surgical site in any appropriate manner, such as through incision and retraction of tissues. In some embodiments, the components of spinal implant system 10 may be used in any existing surgical method or technique including open surgery, mini-open surgery, and minimally invasive surgery including percutaneous surgical implantation. Once access to the surgical site(s) is obtained, the particular surgical procedure is performed for treating the spinal disorder. The components of spinal implant system 10 including fasteners 12 are employed to augment the surgical treatment. Fasteners 12 and one or a plurality of spinal implants, such as, for example, vertebral rods (not shown) can be delivered or implanted as a pre-assembled device or can be assembled in situ. Spinal implant system 10 may be may be completely or partially revised, removed or replaced.

In one embodiment, the components of fastener 12 are assembled, as described herein, prior to implantation. In one embodiment, the components of fastener 12 are assembled, as described herein, in situ. A driver is engaged with shaft 80 until the bit of the driver is disposed in socket 89, as described herein, to rotate shaft 80. The driver is rotated causing fastener 12 to translate axially within a pilot hole of tissue, such as, for example, vertebrae, such that shaft 80 is threaded and engaged with tissue. In some embodiments, fastener 12 is disposed adjacent vertebrae at a surgical site and is manipulated to drive, torque, insert or otherwise connect fastener 12 with the vertebrae.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, system 10 may include one or a plurality of rods, plates, connectors and/or bone fasteners for use with a single vertebral level or a plurality of vertebral levels.

In some embodiments, one or more of fasteners 12 may be engaged with tissue in various orientations, such as, for example, series, parallel, offset, staggered and/or alternate vertebral levels. In some embodiments, one or more of fasteners 12 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, dips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 5:
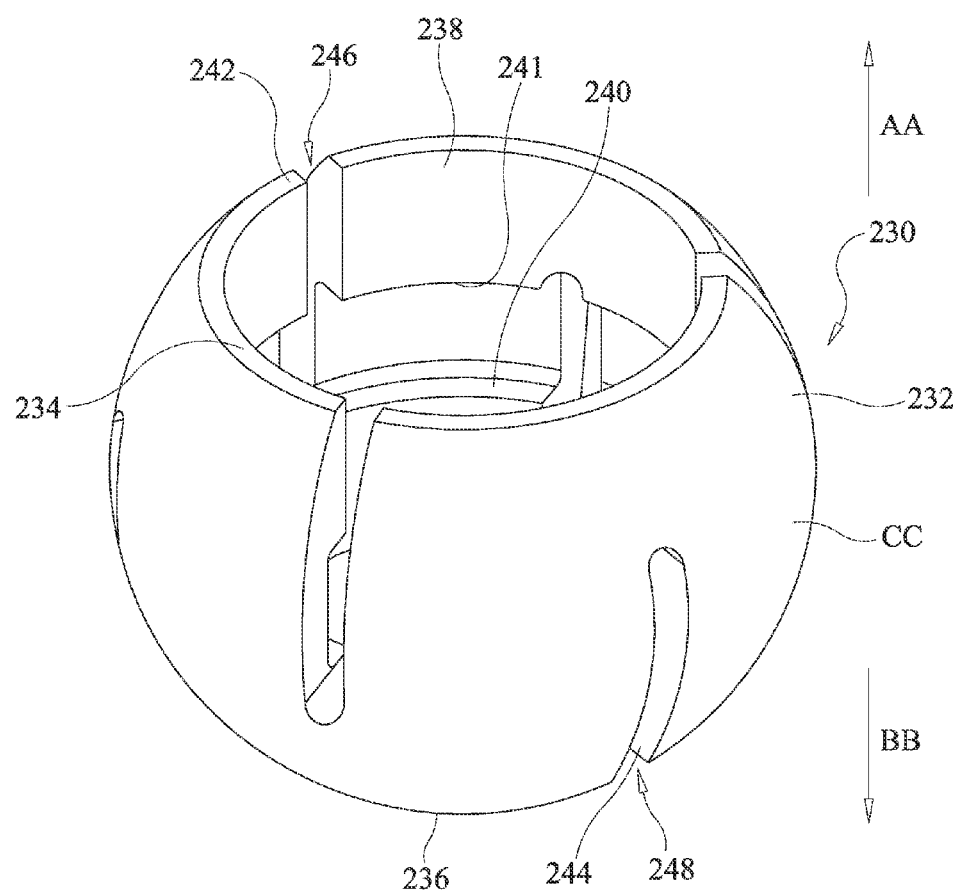
FIG. 5 is a perspective view of components of one embodiment of a spinal implant system in accordance with the principles of the present disclosure.
Figure 6:
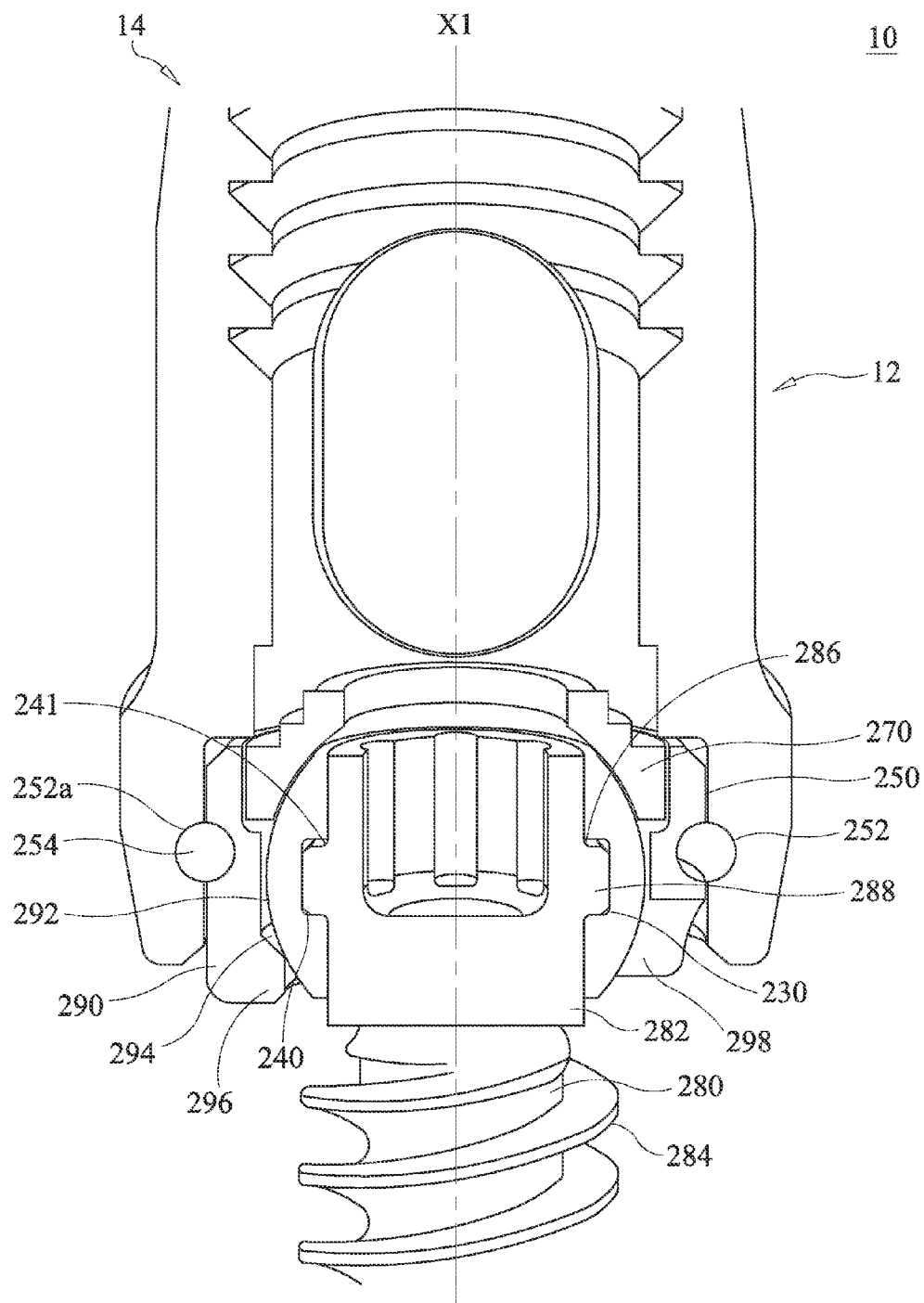
FIG. 6 is a side, cross section view of components of one embodiment of a spinal implant system in accordance with the principles of the present disclosure.

In one embodiment, as shown in FIGS. 5 and 6, system 10, similar to the systems and methods described herein, comprises the sub-assembly, similar to that described herein, of receiver 14 that includes a retainer, such as, for example, a retainer ring 230. Retainer ring 230 and a carrier 290, described herein, are assembled with receiver 14 as a sub-assembly of fastener 12 and for connecting receiver 14 with a shaft 280, similar to shaft 80, described herein.

Retainer ring 230 includes a wall 232, similar to wall 32 described with regard to FIGS. 1, 3 and 4, having an end surface 234 and an end surface 236. Wall 232 includes an inner surface 238 and defines a circumferential flange 240 configured for engagement with a flange 288, as described herein. Surface 238 defines a circumferential flange 241 configured for engagement with flange 288 and spaced from flange 240. Range 288 is disposed with a cavity defined between flanges 240, 241 for fixation of shaft 280 with retainer ring 230.

Shaft 280 includes an end 282 disposed with surface 238 and a threaded end 284, as shown in FIG. 6, configured to penetrate tissue, such as, for example, bone. End 284 is rotatable relative to axis X1, as described herein.

Wall 232 includes a surface that defines a plurality of elongated cavities, such as, for example, slots 242, similar to slots 42 described herein, disposed circumferentially about wall 232. Each of slots 242 extend transversely entirely through a thickness of wall 232. Each of slots 242 extend axially through only a portion of wall 232 in a parallel orientation relative to axis X1. Slots 242 are spaced equidistantly about a circumference CC of wall 232. Slots 242 extend through wall 232 in a U-shaped configuration, in the direction shown by arrow AA in FIG. 5, to an opening, such as, for example, a gap 246 aligned with surface 234. Wall 232 includes a plurality of gaps 246 equidistantly spaced about circumference CC.

The surface of wall 232 also includes a plurality of elongated cavities, such as, for example, slots 244, similar to slots 42 described herein, disposed circumferentially about wall 232. Each of slots 244 extend transversely entirely through the thickness of wall 232. Each of slots 244 extend axially through only a portion of wall 232 in a parallel orientation relative to axis X1 Slots 244 are spaced equidistantly about circumference CC of wall 232. Slots 244 extend through wall 232 in a U-shaped configuration, in the direction shown by arrow BB in FIG. 5, to an opening, such as, for example, a gap 248 aligned with surface 236. Wall 232 includes a plurality of gaps 248 equidistantly spaced about circumference CC. Slots 242 are offset and disposed in axial non-alignment with slots 244.

Retainer ring 230 includes a mating element, such as, for example, surfaces of radial flanges 240, 241 that engage a mating element, such as, for example, one or more surfaces 286 of radial flange 288, as shown in FIG. 6. Retainer ring 230 is disposed with receiver 14, as described herein, in a configuration that facilitates assembly of receiver 14 with shaft 280. In some embodiments, retainer ring 230 engages shaft 280 in a flexible fit, snap fit, interference fit and/or friction fit. Slots 242, 244 provide retainer ring 230 with flexibility so that wall 232 can flex and/or move about flange 288 for disposal of flange 288 with flanges 240, 241 to retain shaft 280 with the sub-assembly, which includes retainer ring 230, of receiver 14. As wall 232 engages shaft 280, surface 238 engages surface 286 such that gaps 246, 248 allow slots 242, 244 to expand. Wall 232 flexes about flange 288 to an expanded orientation such that retainer ring 230 snap fits in a mating engagement with shaft 280. Wall 232 is flexible and resiliently biased to its original orientation for disposal of flange 288 in an abutting engagement with flanges 240, 241. In some embodiments, all or only a portion of retainer ring 230 may have a flexible or elastic configuration, and/or have elastic and/or flexible properties such as the elastic and/or flexible properties corresponding to the material examples described above.

The sub-assembly includes a carrier 290 disposed with receiver 14. Carrier 290 includes an inner surface 292 that defines a cavity 294 configured for disposal of ring retainer 230. Surface 292 includes a flange 296 configured for engagement with ring retainer 230 and retention of ring retainer 230 with carrier 290. Ring retainer 230 rotates within cavity 294 and shaft 280 is guided within cavity 294 to dispose shaft 280 into position for alignment and pivoting into engagement with a concave surface of carrier 290 that defines an opening 298, similar to opening 98 described herein.

Ring retainer 230 and carrier 290 are mounted as a sub-assembly with receiver 14. The sub-assembly is manipulated for assembly with shaft 280 such that ring retainer 230 is assembled with shaft 280, as described herein. A crown 270 of the sub-assembly of receiver 14 is disposable within cavity 294 to engage ring retainer 230 and fix ring retainer 230 with the sub-assembly.

Carrier 290 includes an outer surface 250 that defines a circumferential cavity 252. Surface 250 and receiver 14 define a cavity 252a that is configured for disposal of an elastic ring 254 disposed with receiver 14. Cavity 252 is aligned with a cavity disposed with receiver 14 to enclose ring 254.

In one embodiment, as shown in AG. 7, system 10, similar to the systems and methods described herein, comprises the sub-assembly, similar to that described with regard to FIGS. 5 and 6, of receiver 14 that includes a retainer, such as, for example, a retainer ring 330. Retainer ring 330 and carrier 290, described herein, are assembled with receiver 14 as a sub-assembly of fastener 12 and for connecting receiver 14 with shaft 80, similar to that described herein.

Carrier 330 includes a wall 332, similar to wall 232 described herein, having an end surface 334 and an end surface 336. Wall 332 includes an inner surface 338 and defines a circumferential flange 340 configured for engagement with flange 88, as described herein. Surface 338 defines a circumferential flange 341 configured for engagement with flange 88 and spaced from flange 340. Flange 88 is disposed with a cavity defined between flanges 340, 341 for fixation of shaft 80 with retainer ring 330.

Wall 332 includes a surface that defines a plurality of elongated cavities, such as, for example, slots 342, similar to slots 242, 244 described herein, disposed diametrically about wall 332. Each of slots 342 extend transversely entirely through a thickness of wall 332. Each of slots 342 extend axially entirely through wall 332 in a parallel orientation relative to axis X1. Slots 342 extend through wall 332 to define a gap with surfaces 334, 336. Slots 342 extend entirely through wall 332 such that ring retainer 330 includes a pair of separate ring components 330a, 330b that comprise halves of the retainer that are engaged and/or wrapped about end 82. Components 330a, 330b are disposed about end 82 such that surfaces of radial flanges 340, 341 engage surface 86. Ring retainer 330 is disposed with receiver 14, as described herein, in a configuration that facilitates assembly of receiver 14 with shaft 80.

Ring retainer 330 is manipulated for assembly with shaft 80 such that components 330a, 330b are engaged over end 82. Ring retainer 330 and carrier 290 are mounted as a sub-assembly with receiver 14, similar to that described herein. The sub-assembly is manipulated for assembly with shaft 80 such that ring retainer 330 is assembled with shaft 80, as described herein. Crown 270 of the sub-assembly of receiver 14 is disposable within cavity 294 to engage ring retainer 330 and fix ring retainer 330 with the sub-assembly.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
    a first portion defining a longitudinal axis and including a concave inner surface defining a U-shaped implant cavity;
    a second portion including a first end and a second end configured to penetrate tissue;
    a retainer including a wall having a first end surface and a second end surface, the wall having a maximum diameter adjacent to the first end surface that is equal to a maximum diameter of the wall adjacent to the second end surface, the wall including at least one first elongated cavity and at least one second elongated cavity, the first cavity including a gap that extends through the first end surface without extending through the second end and the second cavity including a gap that extends through the second end surface without extending through the first end surface, the wall further including an inner surface disposed about the first end;
    a crown having a distal end that engages the wall and a proximal end; and
    a carrier comprising a distal end surface that engages the proximal end and a flange that engages a flange of the first portion such that a proximal end surface of the carrier is positioned within the implant cavity.

2. A bone fastener as recited in claim 1, wherein the retainer comprises a carrier having the inner surface directly engage the first end.

3. A bone fastener as recited in claim 1, wherein the wall includes an outer surface that defines a circumferential cavity, the circumferential cavity and the inner surface of the first portion configured for disposal of an elastic ring.

4. A bone fastener as recited in claim 1, wherein the at least one first elongated cavity comprises a plurality of spaced elongated cavities.

5. A bone fastener as recited in claim 1, wherein the at least one first elongated cavity comprises a plurality of spaced elongated cavities and the at least one second elongated cavities comprises a plurality of spaced elongated cavities.

6. A bone fastener as recited in claim 1, wherein the gap of the first end surface is oriented in a first direction and the gap of the second end surface is oriented in a second, opposing direction.

7. A bone fastener as recited in claim 1, wherein the at least one first elongated cavity comprises a plurality of gaps equidistantly spaced about a circumference of the retainer.

8. A bone fastener as recited in claim 1, wherein the second end surface includes a concave surface that defines an opening for disposal of the second end.

9. A bone fastener as recited in claim 8, wherein the concave surface defines a movable limit of the second end.

10. A bone fastener as recited in claim 1, wherein the inner surface of the wall includes a circumferential flange.

11. A bone fastener as recited in claim 1, wherein the elongated cavities are disposed in parallel alignment with the axis.

12. A bone fastener as recited in claim 1, wherein first end comprises a circumferential flange engageable with a circumferential flange of the inner surface of the wall for assembly therewith.

13. A bone fastener as recited in claim 1, wherein the retainer comprises a ring having the inner surface directly engage the first end and an outer surface disposed with a carrier supported with the first portion.

14. A bone fastener as recited in claim 1, wherein the at least one first elongated cavity comprises a plurality of spaced elongated cavities and the at least one second elongated cavities comprises a plurality of spaced elongated cavities, the first elongate cavities being offset and disposed in axial non-alignment with the second elongate cavities.

15. A bone fastener as recited in claim 1, wherein the wall comprises an outer surface opposite the inner surface, the outer surface being concavely curved between the end surfaces.

16. A bone fastener comprising:
    a first portion defining a longitudinal axis and including a concave inner surface defining a U-shaped implant cavity;
    a second portion including a first end and a second end configured to penetrate tissue;
    a retainer including a wall having a first end surface and a second end surface, the wall including at least one first elongated cavity and at least one second elongated cavity, the first cavity including a gap of the first end surface and the second cavity including a gap of the second end surface, the wall further including an inner surface disposed about the first end; and
    a crown having a distal end that engages the wall and a proximal end;
    a carrier that is rotatable relative to the crown, the carrier comprising a distal end surface that engages the proximal end and a flange that engages a flange of the first portion such that a proximal end surface of the carrier is positioned within the implant cavity, the flanges engaging one another to prevent the carrier from moving proximally relative to the first portion,
    wherein the inner surface of the retainer directly engages the first end and an outer surface of the retainer directly engages the first portion.

17. A bone fastener as recited in claim 16, further comprising a ring positioned in a cavity of the first portion and a cavity of the retainer to couple the retainer to the first portion such that the ring is prevented from moving axially relative to the retainer and the first portion.

* * * * *

UNITED STATES PATENT AND TRADEMARK OFFICE
CERTIFICATE OF CORRECTION

PATENT NO. : 9,993,270 B2  
APPLICATION NO. : 14/334970  
DATED : June 12, 2018  
INVENTOR(S) : Butler Page 1 of 1

It is certified that error appears in the above-identified patent and that said Letters Patent is hereby corrected as shown below:

On the Title Page

In Item (72), under "Inventor", in Column 1, Line 1, delete "Brian Butler," and insert
-- Brian A. Butler, --, therefor.

In Column 1, under "Notice", Line 3, delete "0 days. days." and insert -- 0 days. --, therefor.

In the Specification

In Column 5, Line 51, delete "wall 32, Each" and insert -- wall 32. Each --, therefor.

In Column 6, Line 24, delete "avow slots" and insert -- allow slots --, therefor.

In Column 9, Line 3, delete "Range 288" and insert -- Flange 288 --, therefor.

In Column 9, Line 29, delete "X1 Slots" and insert -- X1. Slots --, therefor.

Figure 7:
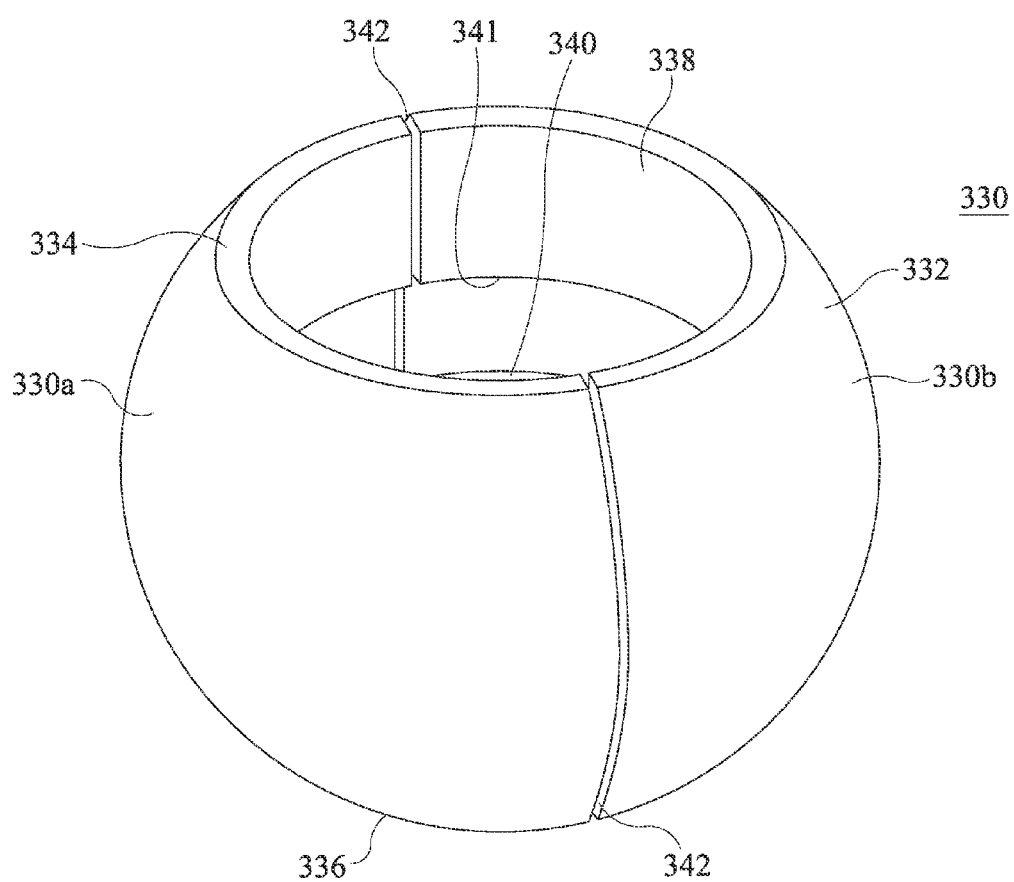
FIG. 7 is a perspective view of components of one embodiment of a spinal implant system in accordance with the principles of the present disclosure.

In Column 10, Line 19, delete "AG. 7," and insert -- FIG. 7, --, therefor.

In the Claims

In Column 12, Line 36, in Claim 16, delete "and" and insert the same at Line 38, after "end;".

Signed and Sealed this
Fourth Day of December, 2018

Andrei Iancu
*Director of the United States Patent and Trademark Office*